US00PP15716P2

(12) United States Plant Patent
Kordes

(10) Patent No.: US PP15,716 P2
(45) Date of Patent: Apr. 12, 2005

(54) MINIATURE ROSE PLANT NAMED 'KORCARILL'

(50) Latin Name: *Rosa hybrida*
Varietal Denomination: KORcarill

(75) Inventor: Tim-Hermann Kordes, Offenseth-Sparrieshoop (DE)

(73) Assignee: W. Kordes' Sŏhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 10/737,637

(22) Filed: Dec. 15, 2003

(30) Foreign Application Priority Data

Apr. 23, 2001 (QZ) ..... PBR 20019999

(51) Int. Cl.[7] ..... A01H 5/00
(52) U.S. Cl. ..... Plt./121
(58) Field of Search ..... Plt./121, 116, 123, Plt./128

(56) References Cited

U.S. PATENT DOCUMENTS

PP11,232 P * 2/2000 Kordes ..... Plt./116
PP11,264 P * 3/2000 Kordes ..... Plt./121

FOREIGN PATENT DOCUMENTS

QZ 20022092 12/2002
QZ 13067 4/2004

* cited by examiner

*Primary Examiner*—Anne Marie Grunberg
*Assistant Examiner*—June Hwu

(57) ABSTRACT

A new and distinct variety of miniature rose with long lasting, novel pink flowers, and dark green and attractive foliage. It exhibits compact, uniform growth and flowering under greenhouse conditions when grown as a potted floral plant. The new variety propagates well from cuttings and by grafting. This new and distinct variety has shown to be uniform and stable in the resulting generations from asexual propagation.

1 Drawing Sheet

Genus, species and variety denomination: The botanical classification of the new rose plant is *Rosa hybrida*, variety denomination 'KORcarill'.

BACKGROUND OF THE INVENTION

The new variety of miniature rose plant of the present invention originated from a controlled crossing in a breeding program between 'KORlusma', a non-patented rose and 'KORkleiva' described and illustrated in U.S. Plant Pat. No. 11,232 issued on Feb. 22, 2000.

The two parents were crossed and the resulting seeds were planted in a controlled greenhouse environment. The resulting seedlings exhibited distinctive physical and biological characteristics. The new rose plant was selected in June, 2000 as a single plant from the seedling beds due to its superior characteristics and asexually propagated for further evaluation. This new and distinctive miniature rose variety is named 'KORcarill'.

SUMMARY OF THE INVENTION

The new rose plant may be distinguished from its seed parent, 'KORlusma', a variety by the same breeder, by the following combination of characteristics:

1. The seed parent has flowers of Red Group 42A, while 'KORcarill' has hot pink colored flowers.
2. The flowers of 'KORcarill' are larger.

The new rose plant may be distinguished from its pollen parent, 'KORkleiva' by the following combination of characteristics:

1. The pollen parent has cream white flowers while 'KORcarill' has hot pink colored flowers.

2. The flower diameter of 'KORcarill' is equal to or slightly larger.

The objective of the hybridization was to create a new and distinct rose plant with unique qualities, such as:

1. Compact and uniform growth and flowering under greenhouse conditions when grown as a potted floral plant;
2. Abundant, long lasting, and attractive flowers on upright stems;
3. Resistance to diseases encountered in greenhouse and nursery culture; and
4. Suitability for production from softwood cuttings in floral and nursery containers;

This combination of traits is not present in prior rose cultivars. These objectives have been substantially achieved and distinguish 'KORcarill' from all other varieties of which we are aware.

As part of the rose development program, Tim-Hermann Kordes germinated the seeds from the aforementioned hybridization and conducted evaluations and observations on the resulting seedlings in a controlled environment in Sparrieshoop, Germany. Asexual reproduction of 'KORcarill' by softwood cuttings was first done Jul. 1, 2000 at the Rosa-Danica Nursery in Odense, Denmark.

This initial and other subsequent propagation conducted in controlled environments show that the foregoing and all other characteristics of 'KORcarill' come true to form and are transmitted through succeeding generations.

BRIEF DESCRIPTION OF THE DRAWING

The accompanying color illustration shows as true as is reasonably possible to obtain in color photographs of this type, the typical characteristics of the buds, flowers, leaves, and stems of 'KORcarill'. Specifically illustrated in SHEET ONE:

1. Tight floral bud;
2. Partially opened flower bud;
3. Half open flower bloom;
4. Flower petals, detached;
5. Sepals, dissected receptacle, and peduncle;
6. Stem exhibiting thorns;
7. Shoot exhibiting anthocyanin coloration;
8. Stem showing branching and the attachment of leaves, and bud;
9. A single leaf; and
10. A single leaf.

DETAILED DESCRIPTION

Figures 1, 2, 3, 4, 5, 6, 7, 8, 9, 10:
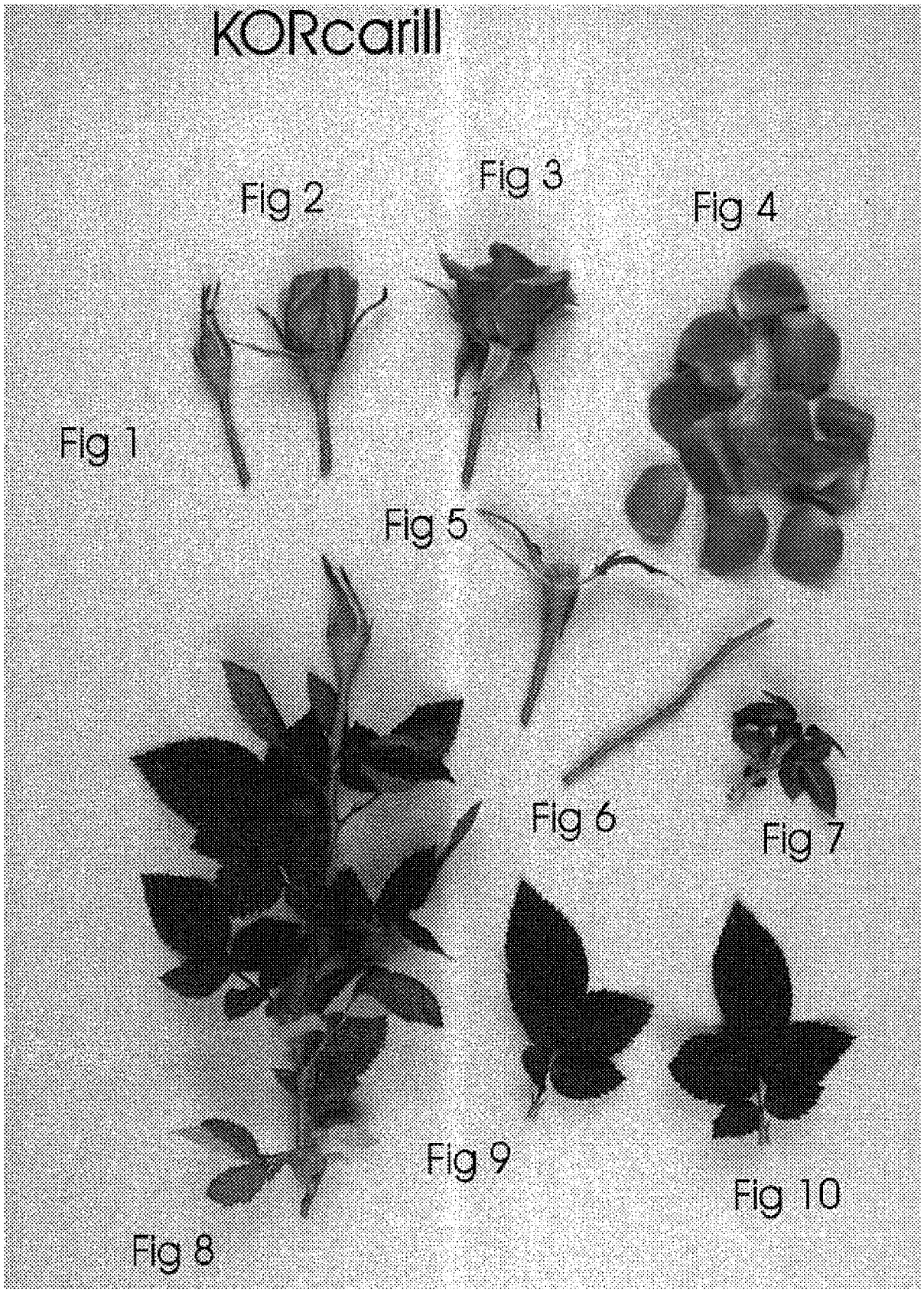

The following is a description of 'KORcarill', as observed in its growth in glasshouses in Odense Denmark on plants of 12 weeks of age and in a field nursery in Sparrieshoop, Germany on plants of 1 year of age. Color references are made using The Royal Horticultural Society (London, England) Colour Chart, 2001 except where common terms of color are used.

For a comparison, several physical characteristics of the rose variety 'KORmisso', a rose variety from the same inventor described and illustrated in U.S. Plant Pat. No. 11,264 and issued on Mar. 7, 2000 are compared to 'KORcarill' in Chart 1.

CHART 1

| Characteristics: | 'KORcariII' | 'KORmisso' |
|---|---|---|
| Flower bloom diameter, | 45–50 mm | 45 mm |
| Petal number | 34–38 petals | 50–60 petals |

Parents:
*Seed parent.*—'KORlusma'.
*Pollen parent.*—'KORkleiva'.

Classification:
*Botanical classification.*—*Rosa hybrida.*
*Commercial classification.*—Miniature.

FLOWER AND FLOWER BUD

Blooming habit: Recurrent.

Flower bud:
*Size.*—Upon opening, 25–30 mm in length from base of receptacle to end of bud.
*Bud form.*—Pointed ovoid.
*Bud color.*—As sepals first unfold, bud color is Red Group 52A. When ¼ open, the upper surface of petals is Red Group 55A, and the lower surface is Red Group 55A.
*Sepals.*—Size: 25 mm long×4–5 mm wide. Margins: Weak to moderate foliaceous appendages on three of the five sepals. Quantity: Five. Surface texture: Surfaces are slightly pubescent. Stipitate glands are present in limited numbers on the margins. Color: Upper surface Green Group 138B. Lower surface Green Group 138A.

Receptacle:
*Surface.*—Smooth. With limited numbers of stipitate glands.
*Color.*—Green Group 146B.
*Shape.*—Funnel shaped.
*Size.*—8–10 mm (h)×10 mm (w).

Peduncle:
*Surface.*—Smooth. Small, fine white hairs and stipitate glands are present.
*Length.*—30–45 mm average length.
*Color.*—Yellow-Green Group 146B.
*Strength.*—Upright and strong. Average Diameter: 1.8–2.0 mm.

Borne: Singly.

Flower bloom:
*Fragrance.*—Light.
*Duration.*—The blooms have a duration on the plant of approximately 21 to 24 days. As a cut flower 10 to 14 days.
*Size.*—Large for a 8–11 cm pot rose. Average flower diameter is 45–50 mm when open.
*Form.*—Shape of flower when viewed from the side: Upon opening, upper part: Convex. Upon opening, lower part: Convex. Open flower, upper part: Convex. Open flower, lower part: Convex.

Color:
*Upon opening, petals.*—Outermost petals: Outer Side: Red Group 58B. Inner Side: Red Group 54B. Innermost petals: Outer Side: Red Group 58B. Inner Side: Red Group 54B–55A.
*Upon opening, basal petal spots.*—Basal petal spot, outermost petals: Outer Side: Yellow Group 1D. Inner Side: Yellow Group 1D. Basal petal spot, innermost petals: Outer Side: Yellow Group 7B. Inner Side: Yellow Group 14B–14D.
*After opening, petals.*—Outermost petals: Outer Side: Red Group 58B. Inner Side: Red Group 54A. Innermost petals: Outer Side: Red Group 58A–58B. Inner Side: Red Group 51B.
*After opening, basal petal spots.*—Basal petal spot, outermost petals: Outer Side: Yellow Group 1D. Inner Side: Yellow Group 1D. Basal petal spot, innermost petals: Outer Side: Yellow Group 7B. Inner Side: Yellow Group 14B–14D. Variegations: None.

General tonality: On open flower Red Group 55A. No change in the general tonality at the end of the $8^{th}$ day. Afterwards, general tonality is Red Group 55B.

Petals:
*Petal count.*—Approximately 34 to 38 petals under normal conditions.
*Petal reflex.*—Petals reflex somewhat.
*Petal edge.*—Entire.
*Petal shape.*—Apex and base are rounded.
*Petal size.*—20–25 mm long; 16–28 mm wide.
*Thickness.*—Average to above average.
*Petal arrangement.*—Generally in a regular pattern with overlapping edges.
*Petaloids.*—Present Quantity: 4–8. Average Size: 6.0–8.0 mm long; 3.0–5.0 mm. wide. Texture: Smooth. Shape: Elliptic.

Reproductive organs:
*Pistils.*—Approximately 50–60 present. Stigmas: Location: Superior in position to anthers. Color: Green-White Group 157A. Styles: Length: 5–8 mm long. Color: Green-White Group 157A. Faint intonations of Greyed-Red Group 181B.
*Stamens.*—Approximately 50–55 on average and regularly arranged around the styles. Anthers: Size: 2 mm long. Color: Yellow Group 14B. Pollen: Limited.

Color: Yellow Group 14B. Filaments: Color: Yellow-Green Group 154C. Limited intonations of Greyed-Red Group 181B. Length: 3–6 mm.

THE PLANT

Plant growth: Vigorous. Upright to bushy. When grown as a 10.5 cm pot plant, the average height of the plant itself is 18–20 cm and the average width is 16–18 cm. When grown as a budded nursery plant the average plant height is 40 cm and the average plant width is 30 cm.

Stems:

*Stem color*.—Young wood: Green Group 138A. Older wood: Green Group 138A.

*Stem surface*.—Young wood: Smooth. Older wood: Smooth.

Prickles: Present.

*Incidence*.—5–6 per 10 cm of stem.

*Size*.—Average length: 6 mm.

*Color*.—Green-White Group 157A, with intonations of Greyed-Red Group 181D.

*Shape*.—Linear.

Leaves and leaflets: Normal leaves in middle of the stem with 5 leaflets.

*Leaf size*.—70–80 mm (l)×50–60 mm (w).

*Quantity*.—Average.

*Glossiness on upper side*.—Moderately glossy.

*Color, mature foliage*.—Upper Leaf Surface: Yellow-Green Group 147A. Lower Leaf Surface: Yellow-Green Group 147B–C.

*Color, juvenile foliage*.—Upper Leaf Surface: Yellow-Green Group 147A. Lower Leaf Surface: Yellow-Green Group 146B–C. Anthocyanin intonation: Present. Intonations present on lower leaflet surface and margins of developing leaves.

Stipules: Size: 8 mm–14 mm.

*Stipule color*.—Yellow-Green Group 147A–B.

*Presence of stipitate glands*.—Limited numbers present on margins.

Petiole:

*Length*.—8 mm–12 mm.

*Diameter*.—1.4 mm–1.6 mm.

*Petiole color*.—Yellow-Green Group 147A–B. Some intonations of Greyed-Red Group 181C, generally on the prickles.

*Prickles*.—Limited number.

*Stipitate glands*.—Present on margins.

Rachis:

*Rachis color*.—Yellow-Green Group 147A–B. Some intonations of Greyed-Red Group 181C, generally on the prickles.

*Prickles*.—Limited number.

*Stipitate glands*.—Present on margins.

Leaflets:

*Terminal leaflet*.—Pointed oval.

*Margins*.—Serrated.

*Texture*.—Average to above average thickness.

*Average size of terminal leaflet*.—35–40 mm long; 25–30 mm wide.

Hips/seed formation: None observed. The plant has not been grown to the stage of hip and seed development due to its use as a flowering potted plant.

Winter hardiness: Due to the variety's principal use in greenhouses, winter hardiness has not been evaluated.

Disease resistance: Above average resistance to mildew and *Botrytis* under normal growing conditions in Odense, Denmark.

I claim:

1. A new and distinct variety of miniature rose plant characterized by the following combination of characteristics:

(a) forms abundant, attractive pink long lasting flowers;

(b) exhibits a compact and bushy growth habit;

(c) is suited for greenhouse culture in pots from softwood cuttings; and;

(d) exhibits durable flowers and foliage suitable for distribution in the floral industry;

substantially as herein illustrated and described.

* * * * *

KORcarill